US006264070B1

(12) United States Patent
McGiveron et al.

(10) Patent No.: US 6,264,070 B1
(45) Date of Patent: Jul. 24, 2001

(54) RESERVOIR PUMP

(75) Inventors: Jeffrey C. McGiveron, Basom; James W. Campbell, Akron, both of NY (US)

(73) Assignee: Cahpin Manufacturing, Inc., Batavia, NY (US)

( * ) Notice: Subject to any disclaimer, the term of this patent is extended or adjusted under 35 U.S.C. 154(b) by 0 days.

(21) Appl. No.: 09/522,697

(22) Filed: Mar. 10, 2000

Related U.S. Application Data

(60) Provisional application No. 60/123,922, filed on Mar. 12, 1999.

(51) Int. Cl.[7] .......................... B67D 5/40; A61M 11/02; B05B 9/04

(52) U.S. Cl. .......................... 222/385; 222/382; 239/373

(58) Field of Search .......................... 222/385, 401, 222/382, 464.1; 239/373, 375

(56) References Cited

U.S. PATENT DOCUMENTS

| | | | | |
|---|---|---|---|---|
| 2,575,508 | * | 11/1951 | Balletto | 222/385 |
| 2,594,223 | * | 6/1952 | Santarelli | 222/385 |
| 6,089,414 | | 7/2000 | Shanklin et al. . | |

* cited by examiner

*Primary Examiner*—Kevin Shaver
*Assistant Examiner*—Stephanie L. Willatt

(74) *Attorney, Agent, or Firm*—Jaeckle Fleischmann & Mugel, LLP

(57) ABSTRACT

A reservoir pump assembly for use with a container having a fill opening and an interior includes an annular, elongate reservoir casing configured for being inserted into the fill opening of the container and for being disposed substantially entirely within the interior of the container. The reservoir casing defines a pressure chamber configured for containing fluid under pressure. An annular, elongate guide cylinder is disposed substantially entirely within the pressure chamber and defines an inlet orifice and an outlet orifice. The outlet orifice interconnects the guide cylinder and the pressure chamber. The inlet orifice interconnects the guide cylinder and the interior of the container. An inlet valve is associated with the inlet orifice, and an outlet valve is associated with the outlet orifice. An elongate pump rod is disposed partially within the guide cylinder and is configured for reciprocating movement therein. The pump rod has a first end and a second end. The first end is disposed within the guide cylinder, and the second end extends from the guide cylinder. A plunger is attached to the first end and is configured for sealingly engaging an inside surface of the guide cylinder. The pump rod is movable in a first direction to draw fluid from the interior of the container into the guide cylinder and movable in a second direction to expel fluid from the guide cylinder into the pressure chamber. A discharge tube is disposed partially within the pressure chamber and defines a passageway for the fluid to exit the pressure chamber.

25 Claims, 10 Drawing Sheets

RESERVOIR PUMP

CROSS REFERENCE TO RELATED APPLICATIONS

This application claims the benefit of U.S. Provisional Application No. 60/123,922, filed Mar. 12, 1999.

BACKGROUND OF THE INVENTION

1. Field of the Invention

The present invention relates to portable, manually operable pump sprayer units for the spraying of liquids or fluids. More particularly, the present invention relates to a manual pump assembly which is received within a conventional liquid container.

2. Description of the Related Art

Portable pump sprayers are typically used for dispensing fluids such as herbicides, cleaning fluids, insecticides, fertilizers, paints, and various other liquids. Conventional portable pump sprayers include a reservoir dimensioned to hold a predetermined volume of liquid, a manual pump assembly which threadingly and sealingly engages a fill opening of the reservoir, a discharge valve, and a spray wand with a nozzle from which the fluid is discharged. The fill opening typically has a minimum diameter of greater than approximately five or six inches and may be as large as approximately twelve inches or greater. The fill opening is typically threaded and receives the manual pump assembly. The manual pump assembly is also threaded and engages the threads of the fill opening. The reservoir of a conventional pump sprayer, in addition to holding the liquid to be sprayed, serves the function of a pressure chamber.

In operation of a conventional pump sprayer, the reservoir/pressure chamber initially contains air at atmospheric pressure and the fluid to be sprayed. The operation of the pump forces air into the reservoir/pressure chamber, thereby increasing the pressure of the air therein to a point substantially greater than atmospheric pressure. The compressed air, in turn, exerts pressure on the fluid contained in the reservoir/pressure chamber. Operation of the discharge valve allows the elevated pressure within the reservoir/pressure chamber to push the fluid out through the nozzle until the valve is closed or equilibrium is reached. The compressed air which exerts pressure on the liquid, however, also exerts that same substantial pressure upon the walls of the reservoir/pressure chamber itself. Thus, the reservoir/pressure chamber must be constructed in a manner and from materials which will withstand and contain the pressure. Therefore, typical reservoirs/pressure chambers are constructed of strong materials, such as stainless steel or aluminum, which are relatively expensive, require special handling and manufacturing techniques, and which are relatively heavy.

Many of the liquids which are ultimately applied by spraying from a portable pump sprayer are distributed and sold to consumers at the retail level in lightweight, thin-walled containers made from plastic. Such containers typically hold a half-gallon or more of liquid. Due to their lightweight construction, the retail containers are not capable of withstanding the substantially elevated internal pressure that is necessary to facilitate the spray application of a liquid from a reservoir. Thus, the retail containers can not perform the function of a pressure chamber. Even if the retail containers were capable of withstanding the internal pressure required for spray application, most manual pump assemblies from conventional pump sprayers are too large to be attached to the small diameter openings found on typical retail containers. Thus, if it is desired to apply by spraying a liquid that is supplied in a typical retail container, a consumer is forced to purchase a separate sprayer unit. The liquid must be poured from the retail container into the sprayer unit and then applied.

An example of a pump unit which includes a pressure chamber that is separate from the reservoir is provided by, for example, U.S. Pat. No. 5,816,454, issued to the present inventor. That pump unit includes a two-part enlarged pressure chamber and a pump. In use, the enlarged pressure chamber is fluidly connected to a reservoir holding fluid to be sprayed. The reservoir may be a conventional container. The enlarged pressure chamber is attached to the reservoir fill opening. The pressure chamber has a diameter that is substantially larger than the reservoir fill opening. Thus, substantially the entire pressure chamber is disposed externally of the reservoir, above the fill opening. The assembly thus formed has several disadvantages.

The disposition of the pressure chamber external to and above the reservoir results in an assembly of substantially larger size and height than the reservoir itself. Thus, the assembly is somewhat cumbersome to carry and manipulate. An impact upon the pressure chamber of the assembly places a great amount of stress on the interface between the pressure chamber and the reservoir to which it is attached. The height of the pressure chamber creates a lever or moment arm which magnifies the stress placed on that interface as a result of any force exerted upon the pressure chamber. The disposition of the pressure chamber external to and above the reservoir, under certain circumstances, creates further disadvantages.

The reservoir may be a conventional liquid container. Such conventional liquid containers are typically of a lightweight construction and will weigh substantially less than a pressure chamber which must be constructed of a more substantial, and therefore heavier, material. When the weight of the volume of liquid in the container is approximately equal to or less than the combined weight of the pressure chamber and any liquid contained therein, the application of a slight force to the pressure chamber will upset and/or topple the assembly. Thus, as the volume of fluid in the container decreases, the degree of instability will progressively increase. Furthermore, the fill opening of a many conventional liquid containers is not disposed on the exact vertical center of gravity of the container. Thus, where a sufficient difference in weight exists between the pressure chamber and a container with an off-center fill opening, the assembly will be inherently unstable. If the assembly is not inherently unstable, any shifting of fluid within the container or within the pressure chamber can result in rendering the assembly unstable and the toppling of the assembly.

The configuration of the assembly also makes operation of the pump cumbersome. When the location of the fill opening does not coincide with the vertical center of gravity of the container, the force exerted on the pump will create a force on the container. This force will have a horizontal component and will act on the container. The horizontal component of that force will be amplified by the pressure chamber acting as a moment arm. Thus, in order to prevent the downward force required to operate the pump from toppling the assembly a user will likely have to stabilize the assembly while pumping.

Moreover, the configuration of the assembly results in a rather unwieldy item from a marketing and distribution standpoint. Packaging, shipping, and displaying the pump unit in an assembled and ready to use configuration is rendered inefficient due to the disposition of the pressure chamber external to and above the container. Specially designed, extra tall shipping containers and a greater spacing between retail display shelves would be required, thereby wasting valuable transportation and display space.

Therefore, what is needed in the art is a manual pump assembly having a pressure chamber which can be disposed substantially entirely within a typical retail liquid container or reservoir.

Furthermore, what is needed in the art is a manual pump assembly for use with a typical retail liquid container or reservoir which is substantially stable when in its use position and during operation.

Moreover, what is needed in the art is a manual pump assembly which is conveniently, efficiently, and easily packaged with a liquid container for distribution and display at the retail level.

SUMMARY OF THE INVENTION

The present invention provides a reservoir pump having an integral pressure chamber which is configured for being disposed substantially entirely within a typical retail liquid container.

A reservoir pump assembly for use with a container having a fill opening and an interior includes an annular, elongate reservoir casing configured for being inserted into the fill opening of the container and for being disposed substantially entirely within the interior of the container. The reservoir casing defines a pressure chamber configured for containing fluid under pressure. An annular, elongate guide cylinder is disposed substantially entirely within the pressure chamber and defines an inlet orifice and an outlet orifice. The outlet orifice interconnects the guide cylinder and the pressure chamber. The inlet orifice interconnects the guide cylinder and the interior of the container. An inlet valve is associated with the inlet orifice, and an outlet valve is associated with the outlet orifice. An elongate pump rod is disposed partially within the guide cylinder and is configured for reciprocating movement therein. The pump rod has a first end and a second end. The first end is disposed within the guide cylinder, and the second end extends from the guide cylinder. A plunger is attached to the first end and is configured for sealingly engaging an inside surface of the guide cylinder, the pump rod is movable in a first direction to draw fluid from the interior of the container into the guide cylinder and movable in a second direction to expel fluid from the guide cylinder into the pressure chamber. A discharge tube is disposed partially within the pressure chamber and defines a passageway for the fluid to exit the pressure chamber. The invention comprises, in another form thereof, a container formed with external, integral storage features which receive and retain the reservoir pump of the present invention and/or a spray hose and wand.

An advantage of the present invention is that the pressure chamber of the reservoir pump is disposed substantially entirely within the liquid container, thereby enabling spraying of liquid from the container without subjecting the container to elevated internal pressure.

Another advantage of the present invention is that it is substantially stable during storage and use.

A further advantage of the present invention is that it may be conveniently shipped, packaged, and sold as a compact and integral unit.

BRIEF DESCRIPTION OF THE DRAWINGS

The above-mentioned and other features and advantages of this invention, and the manner of attaining them, will become apparent and be better understood by reference to the following description of one embodiment of the invention in conjunction with the accompanying drawings, wherein.

The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
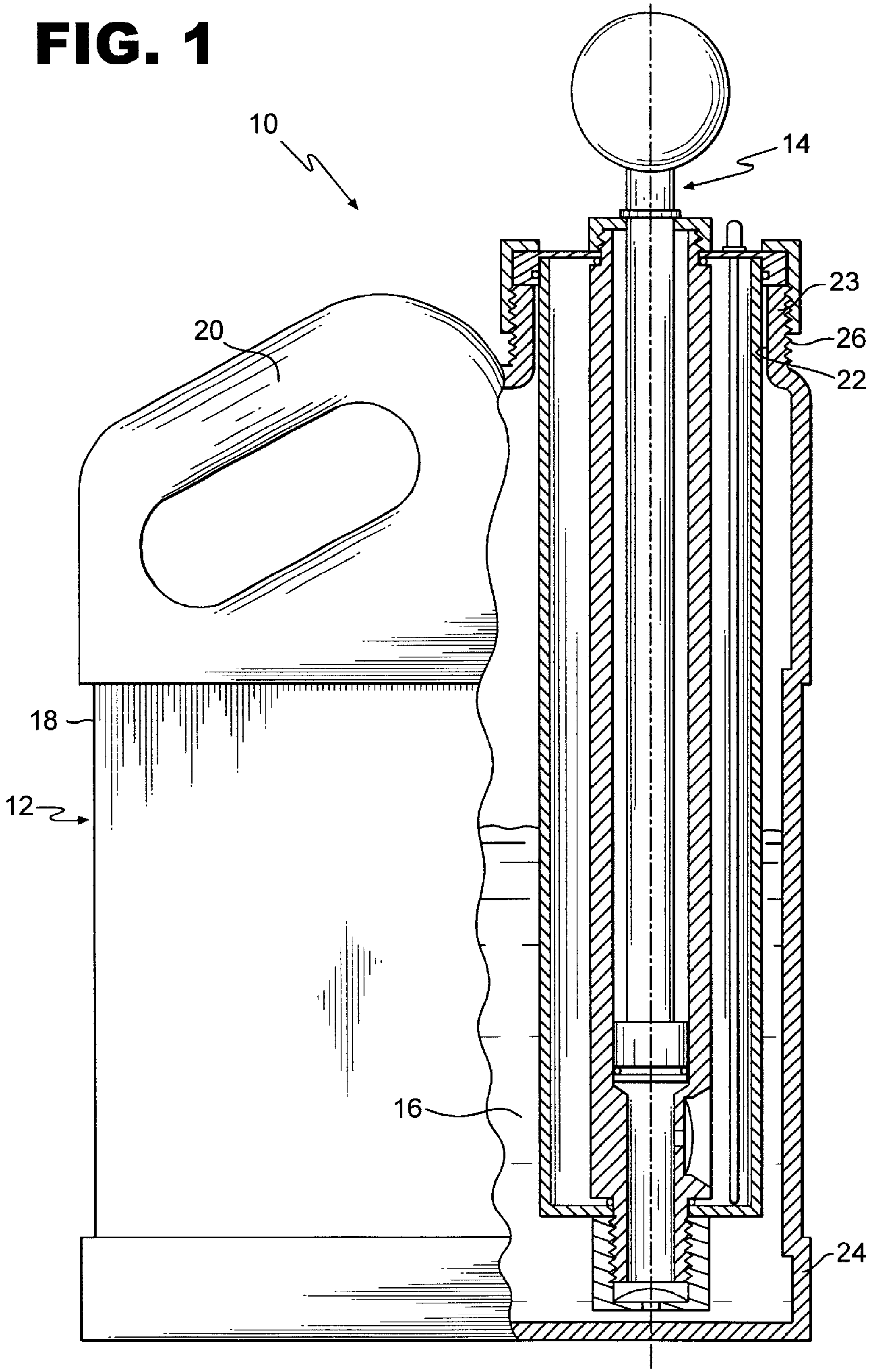
FIG. 1 is a perspective, partially sectioned view of one embodiment of the spray assembly of the present invention.

Referring now to the Figures, and particularly to FIG. 1, there is shown a sprayer assembly 10 of the present invention. Sprayer assembly 10 includes container 12 and manual pump assembly 14. Container 12 holds a quantity of liquid 16 to be applied by spraying. Container 12 includes container body 18, handle 20, opening 22 and base 24. Opening 22 is defined by an annular rim 23 which includes threads 26 formed thereon. Container 12 is filled with liquid 16 by a manufacturer or a user through opening 22. After container 12 has been filled with liquid 16 or after liquid 16 has been dispensed from container 12, a cap (not shown) is used to close and seal container 12. Alternatively, pump assembly 14 is threaded onto rim 23, as hereinafter described, thereby closing and sealing container 12. The interior of container 12 is defined by body 18 rim 23 of fill opening 22, and base 24. Container 12 is constructed of, for example, a lightweight plastic and typically holds a gallon or more of liquid.

Figure 2:
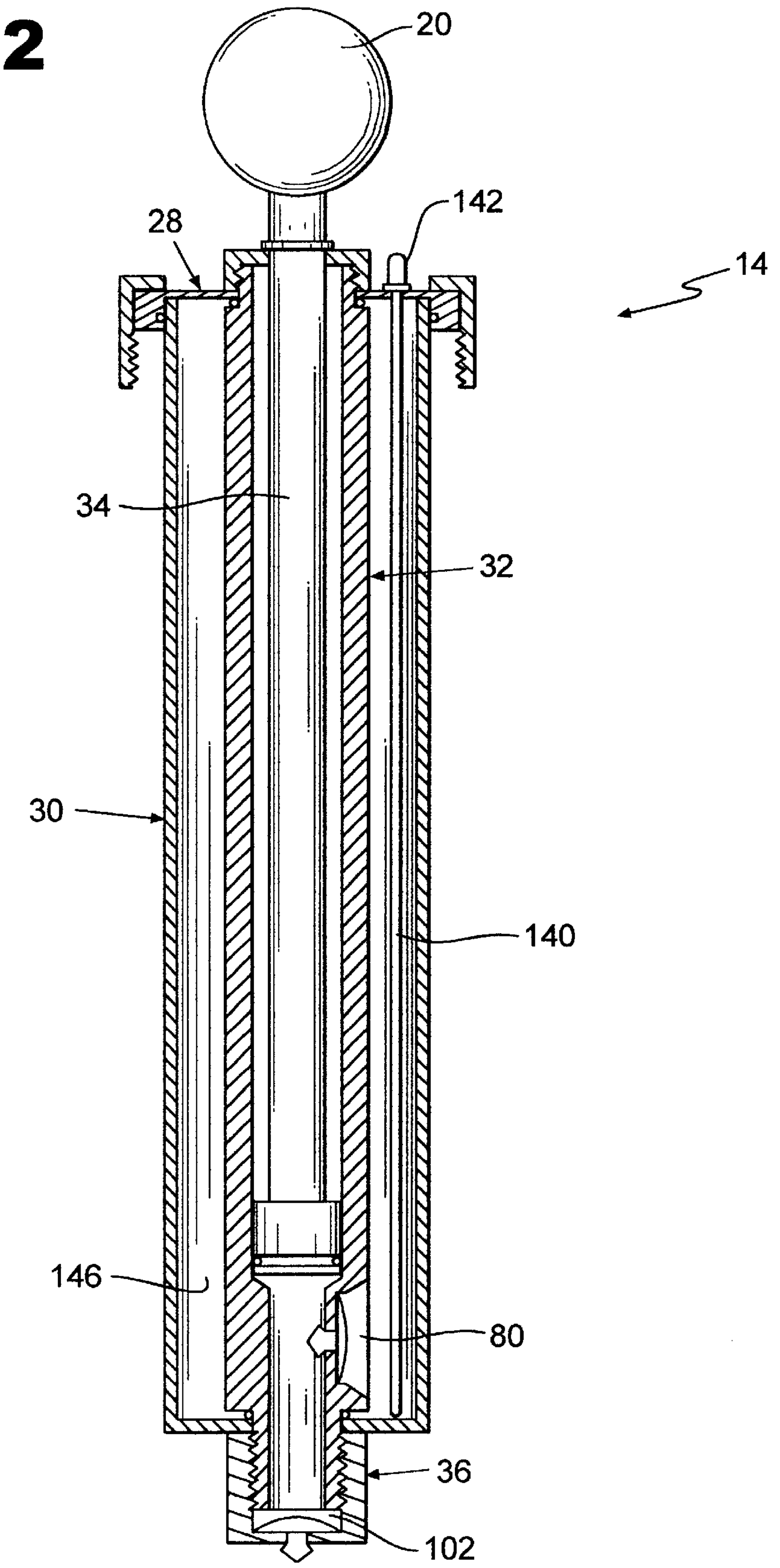
FIG. 2 is a cross-section of the manual reservoir pump assembly of FIG. 1.

Manual pump assembly 14, and the relative configuration of the component parts thereof, is shown in FIG. 2. Pump assembly 14 includes cap 28, reservoir casing 30, pump rod guide cylinder 32, pump rod 34, and end cap 36. Pump rod 34 is disposed concentrically within guide cylinder 32, and guide cylinder 32 is disposed concentrically within reservoir casing 30. Thus, pump rod 34, guide cylinder 32, and reservoir casing 30 are concentric relative to each other.

Figure 3:
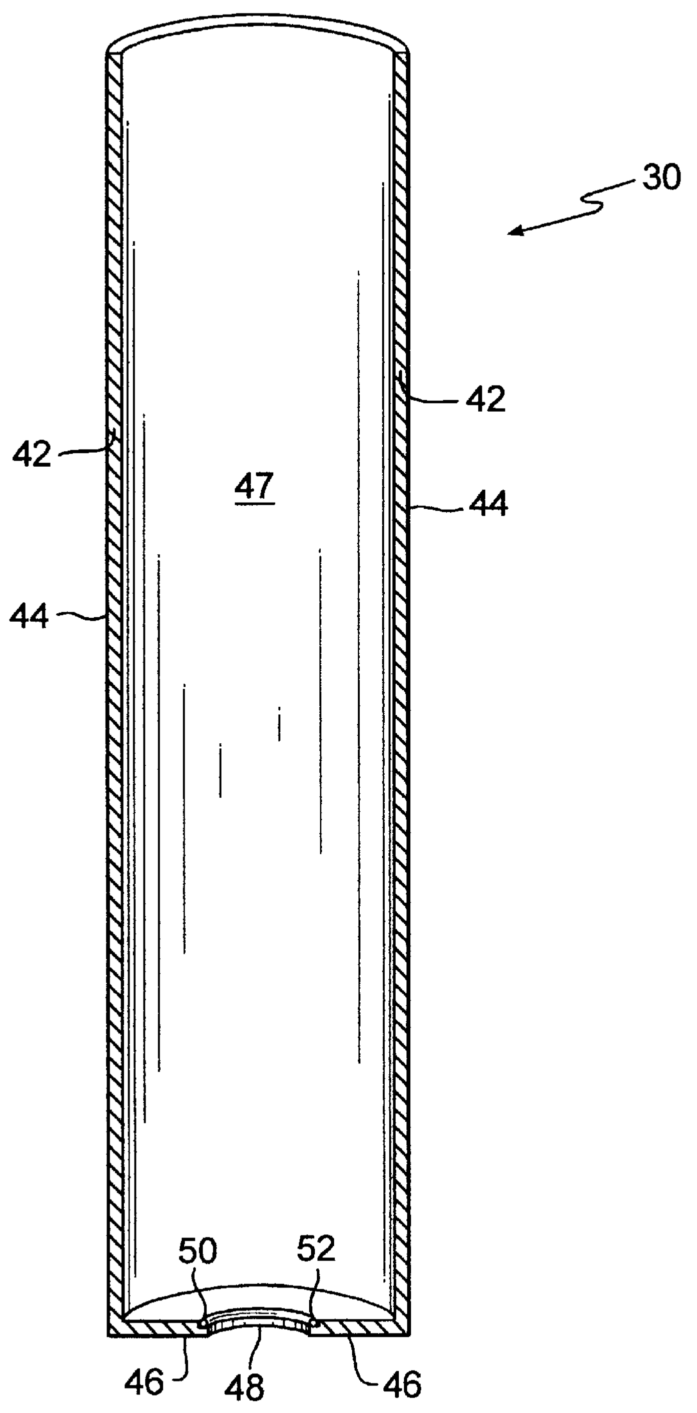
FIG. 3 is a cross-section of the reservoir casing of FIG. 2.

Reservoir casing 30, as best shown in FIG. 3, includes cylindrical side wall 42, having outer surface 44, and bottom wall 46. Side wall 42 and bottom wall 46 conjunctively define pressure chamber 47. Bottom wall 46 defines an aperture 48 therein. A gasket or O-ring 50 surrounds aperture 48 and is seated in groove 52 defined by bottom 46 of reservoir casing 30. O-ring 50 acts to seal reservoir casing 30 together with guide cylinder 32, and is constructed of rubber or fiber. Reservoir casing 30 is constructed of, for example, stainless steel, aluminum, or a highs-strength polymer. Reservoir casing 30 is dimensioned such that it can be inserted through the opening in standard sized liquid containers and be disposed substantially entirely within such standard sized liquid containers.

Figure 4:
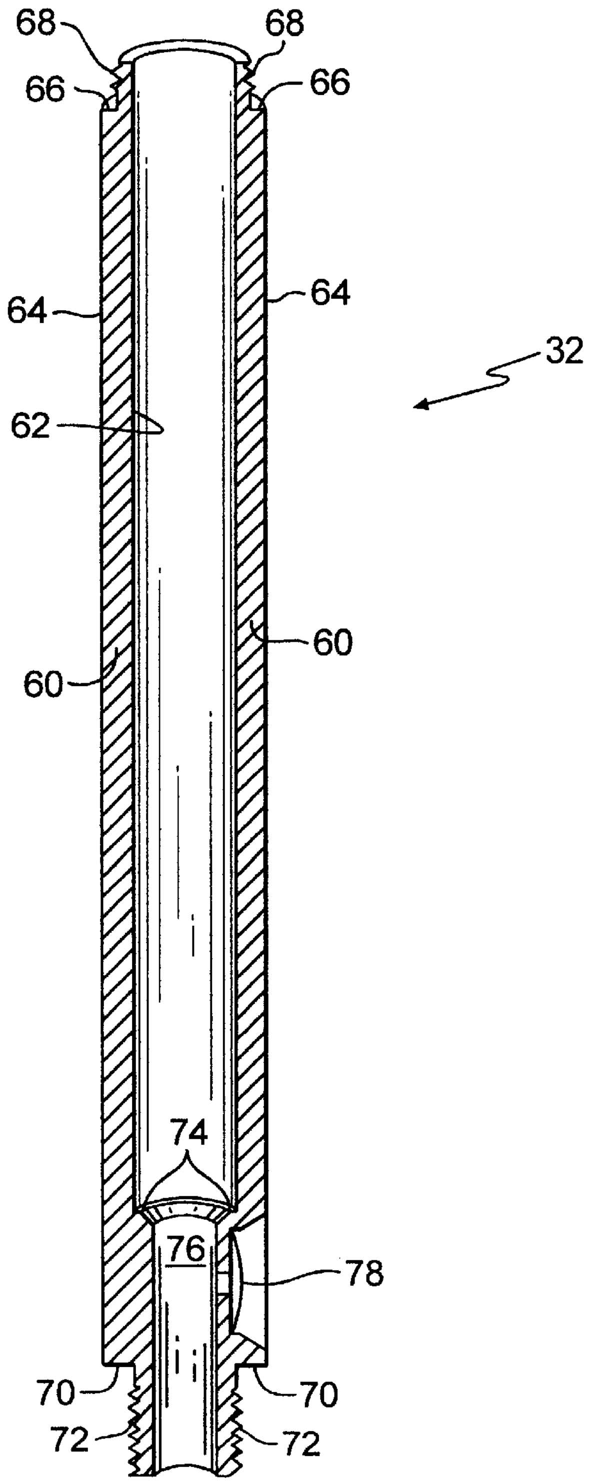
FIG. 4 is a cross-section of the guide cylinder of FIG. 2.

As best shown in FIG. 4, guide cylinder 32 includes a cylindrical side wall 60 having an inside surface 62 and an outside surface 64. At the top end of guide cylinder 32, outside surface 64 of side wall 60 defines top ledge 66 and top threads 68, and at the bottom end of guide cylinder 32 outside surface 64 defines bottom ledge 70 and bottom threads 72. At the bottom end of guide cylinder 32, cylindrical side wall 60 has added interior thickness thereby forming a beveled stop feature 74. A reservoir area 76 is defined by inside surface 62, below stop feature 74. Outside surface 64 of cylindrical side wall 60 defines a seat 78 which receives an outlet valve 80 (FIG. 2). Guide cylinder 32 has a diameter which is somewhat less than the diameter of reservoir casing 30. Guide cylinder 32 is constructed of, for example, stainless steel or aluminum. Guide cylinder 32 guides the reciprocal movement of pump rod 34.

Figure 5:
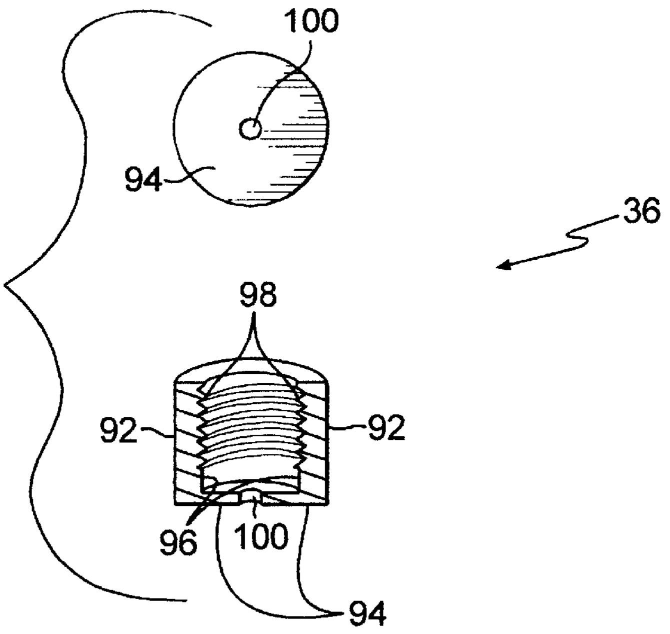
FIG. 5 is a cross-section of the end cap of FIG. 2.

End cap 36, as shown in FIG. 5, includes substantially cylindrical side wall 92 and bottom wall 94. Cylindrical side wall includes interior surface 96, which defines threads 98. Bottom wall 94 defines valve aperture 100. Aperture 100 is sized to receive inlet valve 102 (FIG. 2).

Figure 6:
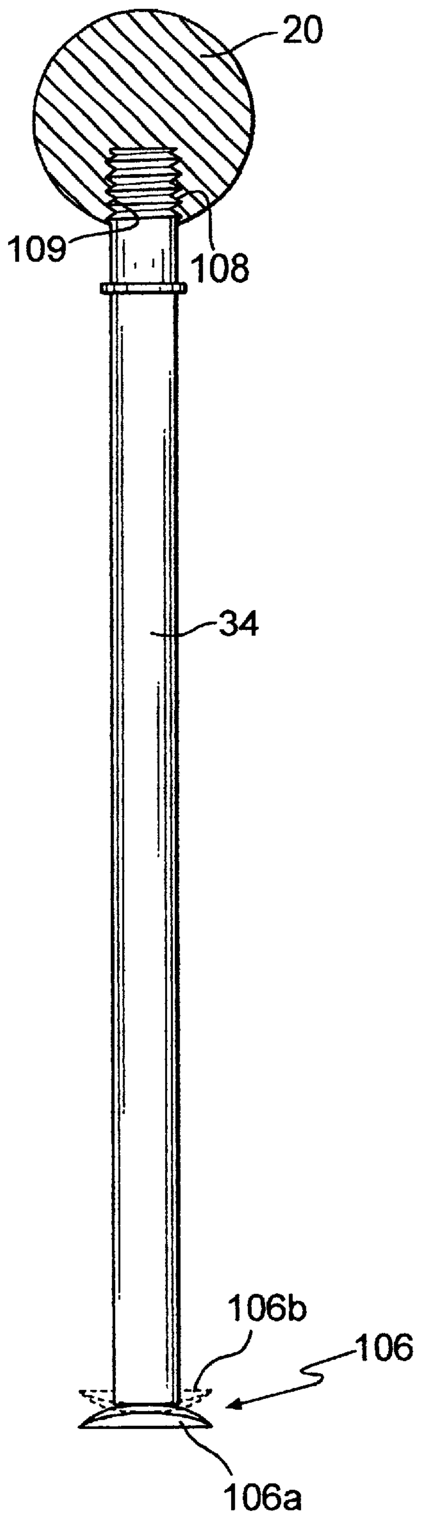
FIG. 6 is a perspective, partially sectioned view of the pump rod assembly of FIG. 2.

Pump rod 34, as best shown in FIG. 6, has attached at one end thereof plunger 106 and defines at the other end thereof threads 108. Threads 109 of handle 20 engage threads 108 of pump rod 34. Pump rod 34 has a diameter which is somewhat less than the diameter of guide cylinder 32. Pump rod 34 is configured for reciprocal motion within guide cylinder 32. Plunger 106 sealingly engages inside surface 62 of guide cylinder side wall 60 during reciprocal motion of pump rod 104.

Figure 7:
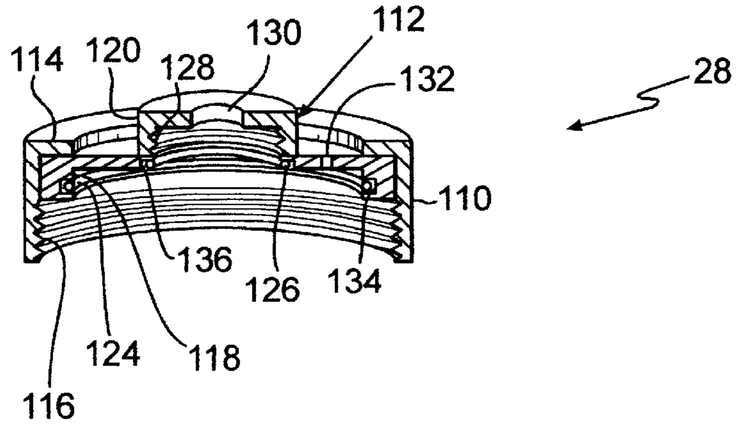
FIG. 7 is a perspective, partially sectioned view of the pump assembly cap of FIG. 2.

Cap 28, as best shown in FIG. 7, includes collar 110 and lid portion 112. Collar 110 includes flange portion 114 and threads 116. Threads 116 are configured to engage threads 26 of opening 22 in container 12. Lid portion 112 includes L-shaped side portion 118 which is interconnected with L-shaped top portion 120. Annular gaskets or O-rings 124 and 126 are associated with and carried by L-shaped side portion 118. L-shape top portion 120 defines threads 128 which threadingly engage top threads 68 formed on side wall 60 of guide cylinder 32. L-shaped top portion further includes an aperture 130 through which pump rod 34 extends. L-shaped side portion 118 of cap 24 defines a discharge opening 132 therein. Seat 134 is defined by L-shaped side portion 118 of lid portion 112. O-ring 124 is received within and retained by seat 134. Similarly, groove 136 is defined by L-shaped side portion 118. Groove 136 receives and retains O-ring 126 therein. Cap 24 is constructed of, for example, a high-strength polymer, stainless steel, aluminum, or other suitable material.

O-ring 124 sealingly engages outer surface 44 of side wall 42 of reservoir casing 30. O-ring 126 sealingly engages top ledge 66 of side wall 60 of guide cylinder 32. O-rings 124 and 126 are constructed of a compressible rubber or fiber material.

Discharge tube 140 (FIG. 2) is an elongate tubular member which is disposed within and extends through discharge opening 132 defined by L-shaped side portion 118 of cap 28. A first end of discharge tube 140 extends a predetermined distance above L-shaped side portion 118. A nipple 142 is attached to discharge tube 140. Discharge tube 140 extends a predetermined distance below L-shaped side portion 118 and into pressure chamber 47 defined by reservoir casing 30. A second end of discharge tube 140 is disposed proximate bottom 46 of reservoir casing 30, thereby maximizing the amount of fluid which can be discharged from pumping chamber 47. Discharge tube 140 is constructed of a rigid plastic, stainless steel or other suitable material.

Handle 20 is a spherical member which defines an aperture 144 having threads 109 which engage threads 108 of pump rod 34. Handle 20 is constructed of, for example, a durable plastic, aluminum or stainless steel. In the embodiment shown, handle 20 is a spherical member. However, it is to be understood that handle 20 may take virtually any shape and may be constructed of any suitable material. For example, handle 20 may be a D-shaped ring member or a T-shaped member that attaches to or threadingly engages pump rod 34. In the embodiment shown, handle 20 and pump rod 34 are threadingly engaged. However, it is to be understood that handle 20 and pump rod 34 may be alternately attached, such as, for example, by epoxy or clamping.

In use, manual pump assembly 14 is assembled by placing guide cylinder 32, carrying outlet valve 80, within pressure chamber 47 such that bottom threads 72 of guide cylinder 32 extend through aperture 48 in reservoir casino 30. Bottom ledge 70 of cylinder 32 engages bottom wall 46 of reservoir casing 30. Bottom ledge 70 also engages O-ring 50. Aperture 48 of reservoir casing 30 is disposed such that guide cylinder 32 will be substantially concentric with reservoir casing 30 when disposed in aperture 48 as described above. End cap 36, carrying inlet valve 102, is threaded onto threads 72 of guide cylinder 32, thereby interconnecting and drawing together reservoir casing 30, guide cylinder 32, and end cap 36.

Pump rod 34 is inserted through aperture 130 in cap 28. Plunger 106 is attached to the end of pump rod 34, and handle 20 is threaded onto threads 108 of pump rod 34. Cap 28, which carries discharge tube 140, is then threaded onto guide cylinder 32 by engaging top threads 128 of cap 28 and top threads 68 of guide cylinder 32 until L-shaped side portion 118 and O-ring 126 engage top ledge 66 of guide cylinder 32. Simultaneously, O-ring 124 carried by L-shaped side portion 118 sealingly engages outer surface 44 of reservoir casing 30. Manual pump assembly 14 is then inserted into fill opening 22 of container 12.

Cap 28 is then placed onto container 12 by engaging threads 116 of cap collar 110 with threads 26 of opening 22 of container 12, thereby drawing collar flange 114 into engagement with L-shaped side 118 of cap 28 and securing cap 28 to container 12. A tubular hose (not shown) terminated with a spray valve (not shown), is then secured to nipple 142. To spray liquid 16 from container 12, pump rod 34 is operated to reciprocally move pump rod 34 up and down within guide cylinder 32. When pump rod 34 is raised, plunger 106 sealingly engages guide cylinder 32 and will deflect into position 106*a* (FIG. 6) and create a vacuum in guide cylinder 32. Inlet valve 102 will open as a result of the vacuum, and liquid 16 will be drawn into reservoir area 76 (FIG. 4) of guide cylinder 32. When the reciprocal motion of pump rod 34 is reversed and moved downward, plunger 106 deflects into position 106*b* (FIG. 6). As pump rod 34 is moved downward, outlet valve 80 opens and liquid 16 is forced from reservoir area 76 into pressure chamber 47. Fluid 16 in pressure chamber 47 compresses air contained therein. When a sufficient amount of fluid 16 has been pumped into pressure chamber 47 and, as a result, sufficient pressure is created within pressure chamber 47, spraying of fluid 16 is initiated by operating the spray valve (not shown) connected to nipple 142. Pressure created by the operation of pump rod 34 is contained entirely within pressure chamber 47, thus preventing the exposure of container 12 to any increased pressure.

Figure 8:
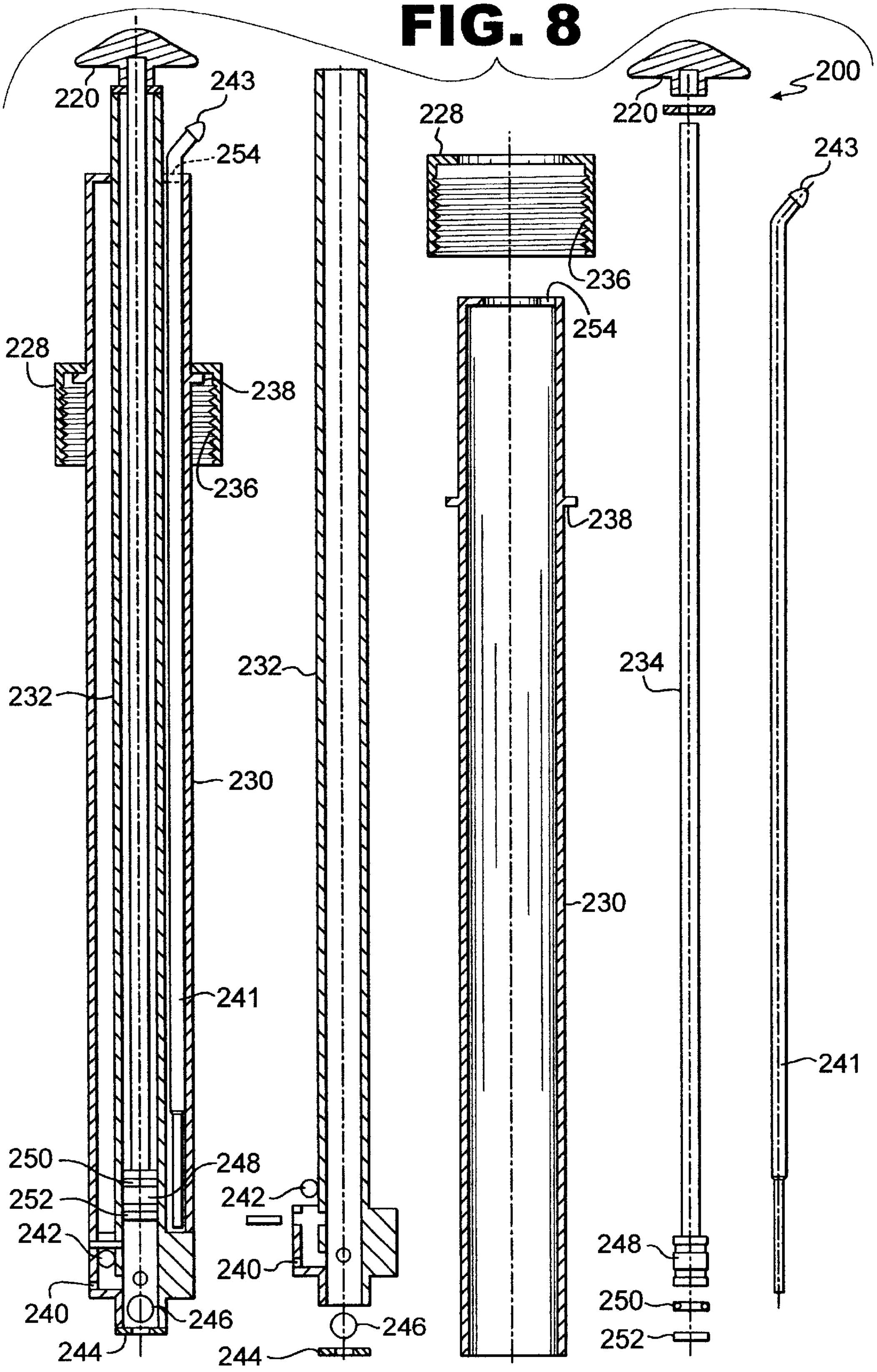
FIG. 8 is a cross-sectional view of a second embodiment of the manual reservoir pump assembly of the present invention.

A second embodiment of the manual pump assembly of the present invention is shown in FIG. 8. Manual pump assembly 200 is constructed similar to and operates using the same principles as manual pump assembly 14. Manual pump assembly 200 includes handle 220, cap 228, reservoir casing 230, guide cylinder 232, and pump rod 234. Cap 228 of manual pump assembly 200 is a one-piece cap, rather than the two piece construction of manual pump assembly 14. Threads 236 of cap 228 engage opening 22 of container 16 from which liquid is to be sprayed. Reservoir casing 230 includes a flange 238 which is engaged by cap 228 when manual pump assembly 200 is in its use position. Guide cylinder 232 includes seat 240 formed integral therewith to receive a ball-type check valve 242, and a seat 244 for ball-type check valve 246. Pump rod 234 includes plunger 248. Plunger 248 is attached to pump rod 234 by clamp 250, which may be configured as, for example, a ring clamp or a deformable C-clamp. O-ring 252 sealingly engages the inner wall of guide cylinder 232 during reciprocal motion of pump rod 234 within guide cylinder 232. Discharge tube 256 is sealingly received in and extends through aperture 254 defined by reservoir casing 230. Nipple 243 is formed integrally with discharge tube 241. In use, manual pump assembly 200 operates substantially the same as manual pump assembly 14, as described hereinabove.

Figure 9:
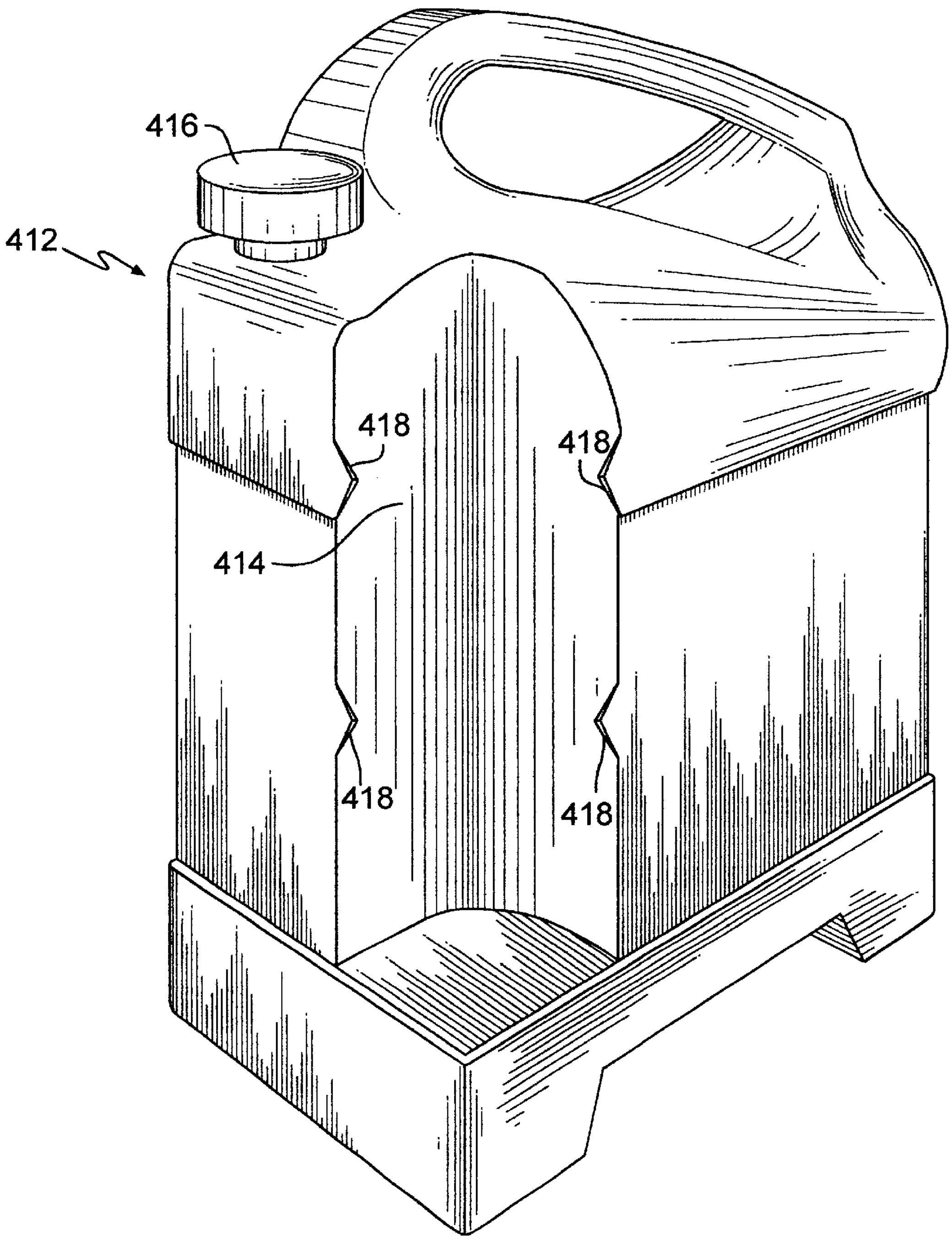
FIG. 9 is a perspective view of one embodiment of the container of the present invention.
Figure 10:
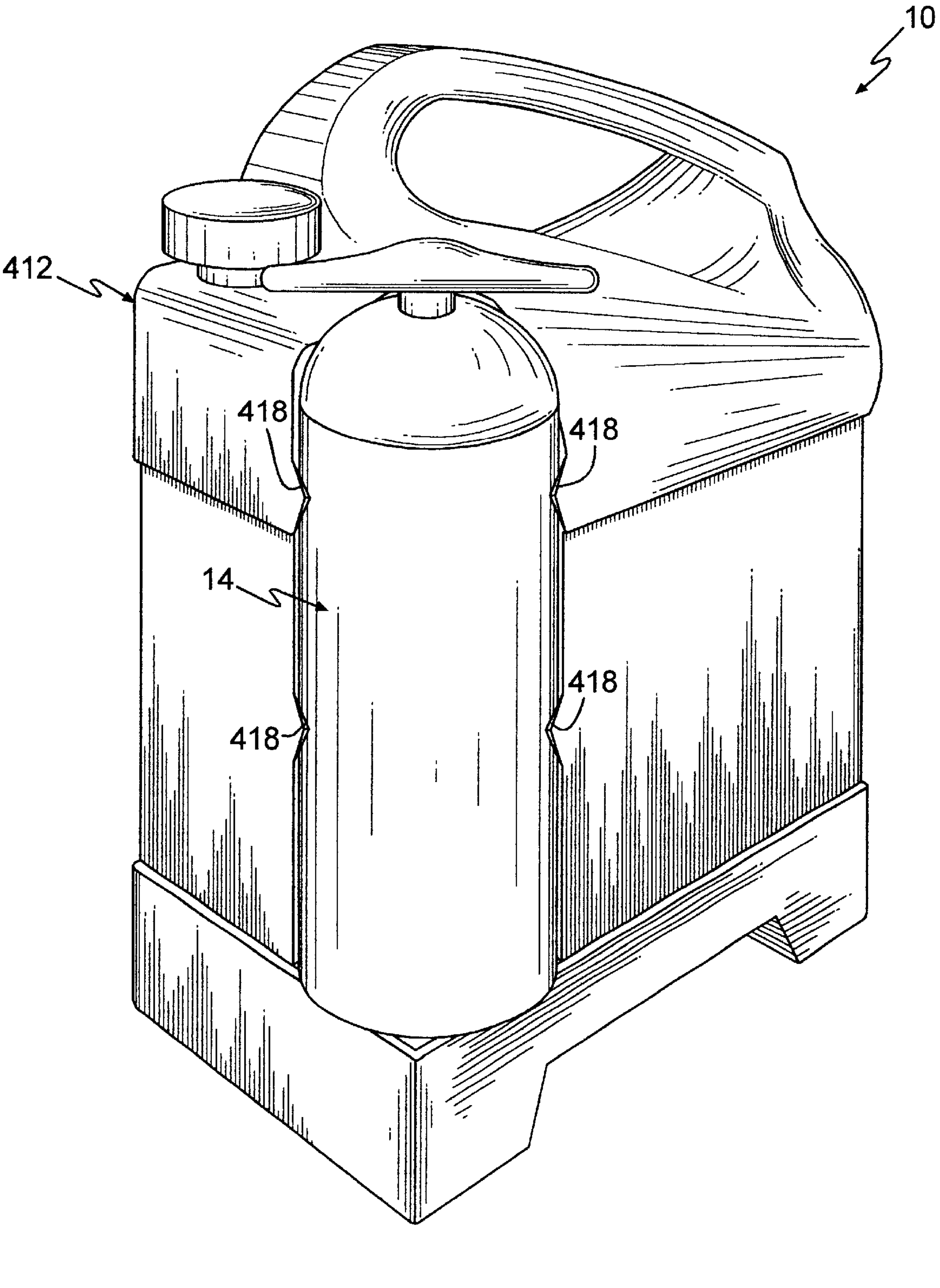
FIG. 10 is a perspective view of the reservoir pump assembly of the present invention and the container of FIG. 9.

A second embodiment of the container of the sprayer assembly 10 of the present invention is shown in FIG. 9. Container 412 includes indentation 414, cap 416 and snap features 418. As shown in FIG. 10, indentation 414 receives and stores manual pump assembly 14. Snap features 418 are formed integrally with container 412 and deform to receive and retain manual pump assembly 14 within indentation 414. Thus, container 412 facilitates shipping, distribution and merchandising of sprayer assembly 10 by creating a single integrated, convenient, space-saving, and attractive package therefor.

Figure 11:
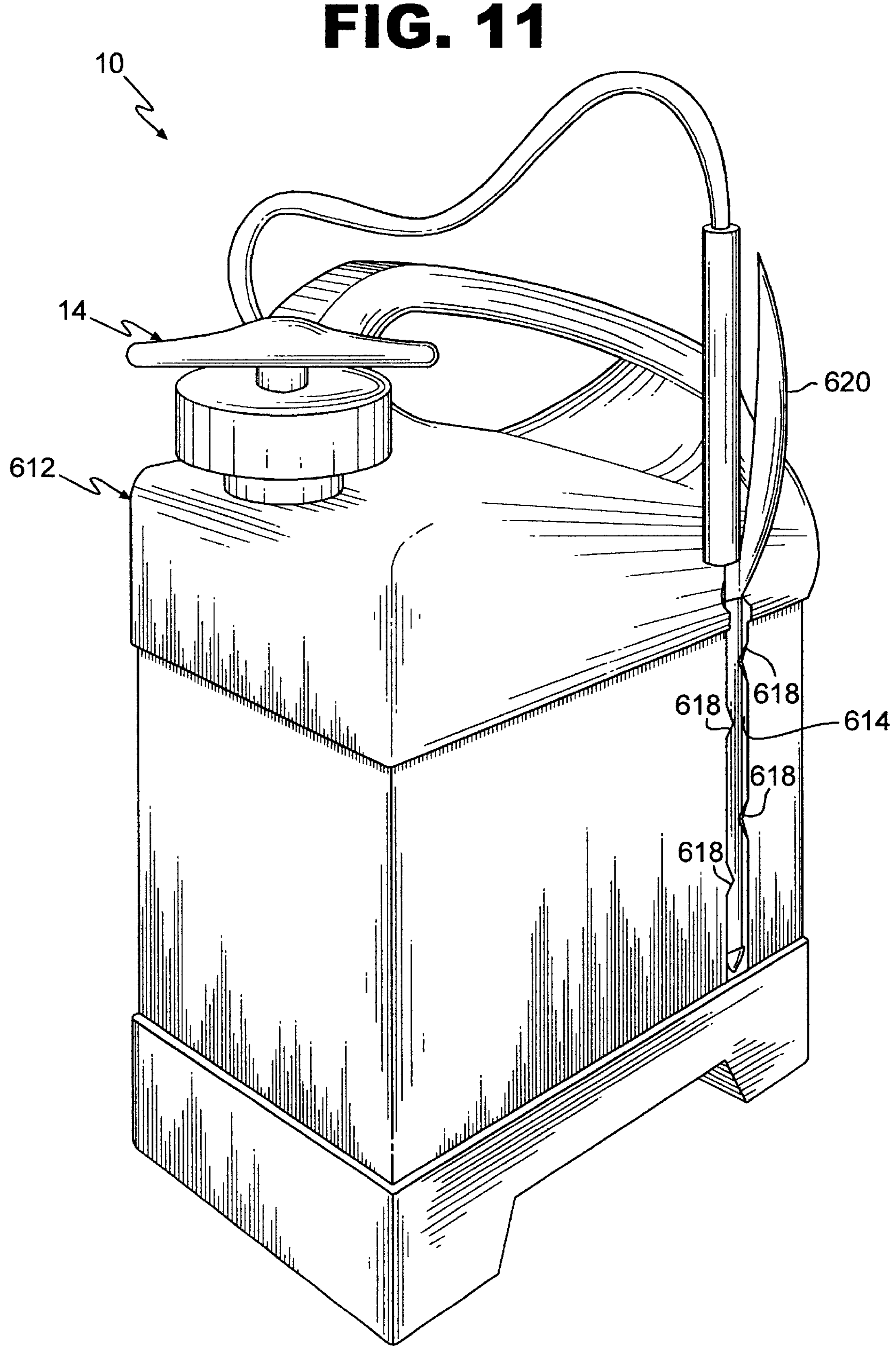
FIG. 11 is a perspective view of a third embodiment of the container of the present invention.

A still further embodiment of the container of sprayer assembly 10 of the present inventions is shown in FIG. 11. Container 612 includes indentation 614 which receives discharge hose 618 and spray wand 620. Snap features 622 are formed integral with container 612 and adjacent to indentation 614, and are configured to removably retain discharge hose 618 and spray wand 620 during shipping and display of container 612.

In the embodiment shown, side wall 42 of reservoir casing 30, side wall 60 of guide cylinder 32 and side wall 92 of end cap 36 are described as cylindrical. However, it is to be understood that side wall 42, side wall 60 and side wall 92 may be alternately configured, such as, for example, having an oval or rectangular shape.

In the embodiment shown, cap 28 is described as having a lid portion 112 including two L-shaped portions, side portion 118 and top portion 120, which are interconnected. However, it is to be understood that side portion 1 18 and top portion 120 may be alternately configured, such as, for example, as an integral lid portion 112.

While this invention has been described as having a preferred design, the present invention can be further modified within the spirit and scope of this disclosure. This application is therefore intended to cover any variations, uses, or adaptations of the present invention using the general principles disclosed herein. Further, this application is intended to cover such departures from the present disclosure as come within the known or customary practice in the art to which this invention pertains and which fall within the limits of the appended claims.

What is claimed:

1. A reservoir pump assembly for use with a container having a fill opening and an interior, said reservoir pump assembly comprising:

an annular, elongate reservoir casing configured for being inserted into the fill opening in the container and for being disposed substantially entirely within the interior of the container, said reservoir casing defining a pressure chamber configured for containing fluid under pressure;

an annular, elongate guide cylinder, said guide cylinder being disposed substantially entirely within said pressure chamber, said guide cylinder defining an inlet orifice and an outlet orifice, said outlet orifice interconnecting said guide cylinder and said pressure chamber, said inlet orifice interconnecting said guide cylinder and the interior of the container, an inlet valve associated with said inlet orifice, an outlet valve associated with said outlet orifice;

an elongate pump rod disposed partially within said guide cylinder and being configured for reciprocating movement therein, said pump rod having a first end and a second end, said first end being disposed within said guide cylinder, said second end of said pump rod extending from said guide cylinder, a plunger being attached to said first end, said plunger configured for sealingly engaging an inside surface of said guide cylinder at least during reciprocal movement of said pump rod, said pump rod being movable in a first direction to draw fluid from the interior of the container into said guide cylinder and movable in a second direction to expel fluid from said guide cylinder into said pressure chamber; and a discharge tube disposed at least partially within said pressure chamber, said discharge tube defining a passageway for the fluid to exit said pressure chamber.

2. The reservoir pump assembly of claim 1, further comprising a cap configured for sealingly engaging the fill opening of the container and said reservoir casing.

3. The reservoir pump assembly of claim 2, wherein said cap includes threads, said threads configured for threadingly engaging corresponding threads on the fill opening of the container.

4. The reservoir pump assembly of claim 2, wherein said cap defines a discharge tube orifice, said discharge tube extending through said discharge tube orifice.

5. The reservoir pump assembly of claim 2, wherein said cap comprises a lid portion and a collar portion, said collar portion of said cap including collar threads, said collar portion being configured for threadingly engaging the threads of the fill opening of the container, said collar portion further including a flange portion configured to engage said lid portion as said collar portion is threaded onto the fill opening.

6. The reservoir pump assembly of claim 5, wherein said lid portion includes lid threads, said first end of said guide cylinder including threads, said lid portion being configured to threadingly engage said first end of said guide cylinder.

7. The reservoir pump assembly of claim 6, wherein said first end of said guide cylinder defines a top ledge therein, said lid portion of said cap threadingly engaging said first end of said guide cylinder until said lid portion engages said top ledge.

8. The reservoir pump assembly of claim 5, wherein said lid portion includes a yoke, said yoke configured to sealingly engage said reservoir casing.

9. The reservoir pump assembly of claim 8, wherein an O-ring is disposed around said yoke.

10. The reservoir pump assembly of claim 9, wherein said yoke defines a groove, said O-ring being disposed at least partially within said groove.

11. The reservoir pump assembly of claim 1, further comprising an end cap, each of said reservoir casing and said guide cylinder including a respective second end, said second end of said reservoir casing defining a guide cylinder aperture therein, said second end of said guide cylinder defining a lower ledge configure to engage said reservoir casing adjacent said guide cylinder aperture, said second end of said guide cylinder extending through said guide cylinder aperture, said end cap defining an end cap inlet aperture therein, said end cap being attached to said guide cylinder and engaging said reservoir casing such that said end cap inlet aperture is in fluid communication with said inlet orifice of said guide cylinder.

12. The reservoir pump assembly of claim 11, wherein said second end of said guide cylinder includes threads, said end cap including end cap threads on an interior surface thereof and being configured to threadingly engage said guide cylinder, thereby drawing said lower ledge of said second end of said guide cylinder into contact with said reservoir casing.

13. The reservoir pump assembly of claim 11, wherein said reservoir casing includes an O-ring surrounding said guide cylinder aperture .

14. The reservoir pump assembly of claim 13, wherein said reservoir casing includes a groove formed adjacent said guide cylinder aperture, said O-ring being disposed at least partially within said groove.

15. The reservoir pump assembly of claim 1, wherein said guide cylinder is substantially concentric with said reservoir casing.

16. The reservoir pump assembly of claim 1, further comprising a handle attached to said pump rod.

17. A sprayer assembly, comprising:

a container including a body and an annular rim defining a fill opening, an interior of said container being defined by said body and said annular rim; and a reservoir pump assembly comprising:

a cap configured for sealingly engaging said annular rim of said fill opening, said cap defining a pump rod aperture therein;

an annular, elongate reservoir casing having a first end associated with said cap, said reservoir casing configured for being inserted through said fill opening and being disposed substantially entirely within said interior, said reservoir casing defining a pressure chamber configured for containing fluid under pressure;

an annular, elongate guide cylinder having a first end associated with said cap, said guide cylinder being disposed substantially entirely within said pressure chamber, said guide cylinder defining an inlet orifice and an outlet orifice, said outlet orifice interconnecting said guide cylinder and said pressure chamber, said inlet orifice interconnecting said guide cylinder and said interior of said container, an inlet valve associated with said inlet orifice, an outlet valve associated with said outlet orifice;

an elongate pump rod disposed partially within said guide cylinder and configured for reciprocating movement therein, said pump rod including a first end and a second end, said first end being disposed within said guide cylinder, said second end extending through said pump rod aperture in said cap, a plunger attached to said first end, said plunger configured for sealingly engaging, an inside surface of said guide cylinder at least during reciprocal movement of said pump rod, said pump rod being movable in a first direction to draw fluid from said interior of said container into said guide cylinder and movable in a second direction to expel fluid from said guide cylinder into said pressure chamber, and a discharge tube disposed at least partially within said pressure chamber, said discharge tube defining a passageway for the fluid to exit said pressure chamber.

18. The sprayer assembly of claim 17, wherein said fill opening is threaded, said cap including threads complementary to said fill opening threads, said cap being configured to threadingly engage said fill opening.

19. The sprayer assembly of claim 17, wherein said cap defines a discharge tube orifice, said discharge tube extending through said discharge tube orifice.

20. The sprayer assembly of claim 17, wherein said cap guide cylinder is substantially concentric with said reservoir casing.

21. The sprayer assembly of claim 17, wherein said pressure chamber is disposed substantially entirely within said interior of said container.

22. The sprayer assembly of claim 17, further comprising a handle attached to said pump rod.

23. The sprayer assembly of claim 17, wherein said container includes a first indented portion configured for receiving said reservoir pump assembly, at least one retaining member disposed adjacent said first indented portion and being configured for removably retaining said reservoir pump assembly within said indented portion.

24. The sprayer assembly of claim 23, wherein said at least one retaining member is integral and monolithic with said container.

25. The sprayer assembly of claim 17, wherein said container includes at least one second indented portion configured for receiving at least one of a spray hose and spray wand, at least one retaining member disposed adjacent each said at least one second indented portion and being configured for removably retaining a respective one of the spray hose and spray wand within said second indented portion.

* * * * *

UNITED STATES PATENT AND TRADEMARK OFFICE

CERTIFICATE OF CORRECTION

PATENT NO. : 6,264,070 B1
DATED : July 24, 2001
INVENTOR(S) : Jeffrey C. McGiveron and James W. Campbell It is certified that error appears in the above-identified patent and that said Letters Patent is hereby corrected as shown below:

Title page,
Item [73] should read "Chapin Manufacturing, Inc."

Signed and Sealed this

Fifth Day of February, 2002

*Attest:*

JAMES E. ROGAN
*Director of the United States Patent and Trademark Office*

*Attesting Officer*